(12) United States Patent
Blacklock

(10) Patent No.: US 6,913,463 B2
(45) Date of Patent: Jul. 5, 2005

(54) DRILLING GUIDE FOR DENTAL IMPLANTATION

(76) Inventor: Gordon D. Blacklock, 14116 Grand Northeast, Albequerque, NM (US) 87123

( * ) Notice: Subject to any disclaimer, the term of this patent is extended or adjusted under 35 U.S.C. 154(b) by 162 days.

(21) Appl. No.: 10/078,002

(22) Filed: Feb. 20, 2002

(65) Prior Publication Data
US 2003/0157457 A1 Aug. 21, 2003

(51) Int. Cl.[7] .............................................. A61C 13/38
(52) U.S. Cl. .............................. 433/72; 433/76; 606/96; 408/115 R
(58) Field of Search ............................. 433/72, 74, 75, 433/76; 606/96, 95; 408/115 R, 115 B, 72 R, 72 B

(56) References Cited

U.S. PATENT DOCUMENTS

| | | | | |
|---|---|---|---|---|
| 2,181,746 A | * | 11/1939 | Siebrandt ..................... 606/96 |
| 4,045,874 A | | 9/1977 | Roman | |
| 4,306,866 A | | 12/1981 | Weissman | |
| 4,325,373 A | * | 4/1982 | Slivenko et al. .............. 606/96 |
| 4,450,835 A | * | 5/1984 | Asnis et al. ................... 606/73 |
| 5,015,183 A | * | 5/1991 | Fenick .......................... 433/76 |
| 5,133,660 A | * | 7/1992 | Fenick .......................... 433/76 |
| 5,306,278 A | * | 4/1994 | Dahl et al. ..................... 606/96 |
| 5,320,529 A | * | 6/1994 | Pompa .......................... 433/76 |
| 5,688,283 A | * | 11/1997 | Knapp .......................... 606/96 |
| 5,718,579 A | * | 2/1998 | Kennedy ....................... 433/75 |
| 5,769,636 A | * | 6/1998 | Di Sario ....................... 433/213 |
| 5,800,168 A | * | 9/1998 | Cascione et al. ............. 433/75 |
| 5,833,693 A | | 11/1998 | Abrahami | |
| 5,851,207 A | | 12/1998 | Cesarone | |
| 5,967,777 A | * | 10/1999 | Klein et al. ................... 433/75 |
| 6,296,483 B1 | * | 10/2001 | Champleboux .............. 433/75 |

* cited by examiner

Primary Examiner—Ralph A. Lewis
(74) Attorney, Agent, or Firm—Siemens Patent Services LC

(57) ABSTRACT

An adjustable drilling guide, removably mountable to a patient's teeth, having a guide block with at least one stent for guiding a dental drill is disclosed. In a first embodiment, the guide block has a plurality of guide holes disposed at differing angles which may receive a stent for precise drilling at the selected angle. If minor variations need be made, the stent may be moved to a second or third of the guide holes to adjust the angle. In a second embodiment, three distinct stents are formed directly in the guide block allowing for drilling at up to three different angles. A third embodiment has a stent which is pivotable about a pivot point within the guide block, allowing drilling at any angle within the arc of the pivot. The guide block may be fitted to a model of the patient's teeth prior to installation into the mouth to ensure proper fit.

5 Claims, 4 Drawing Sheets

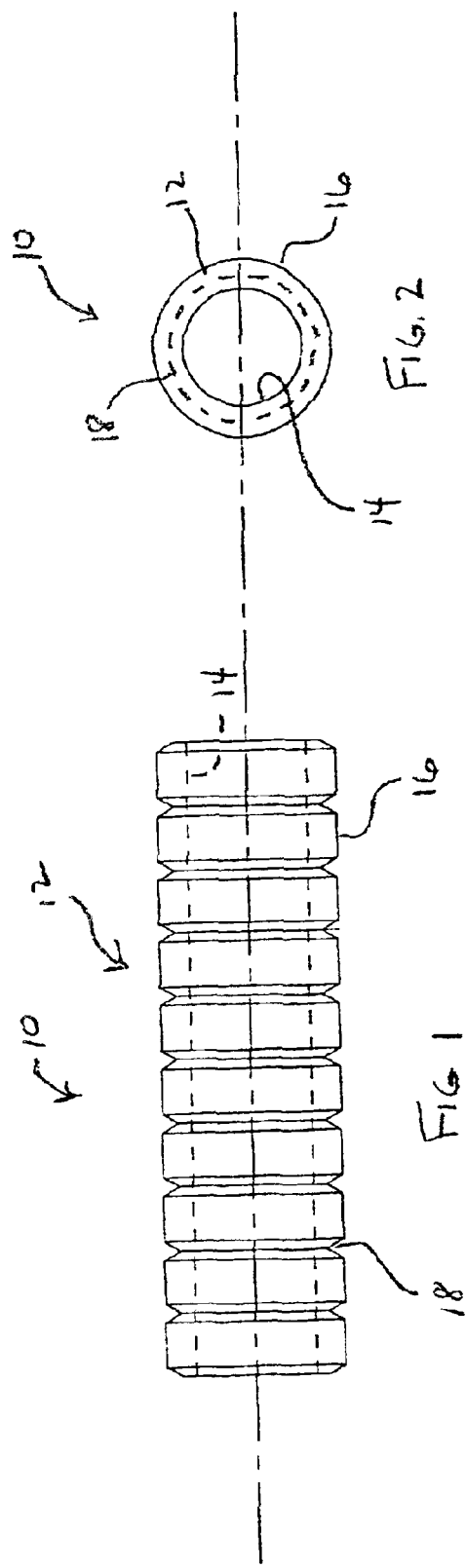

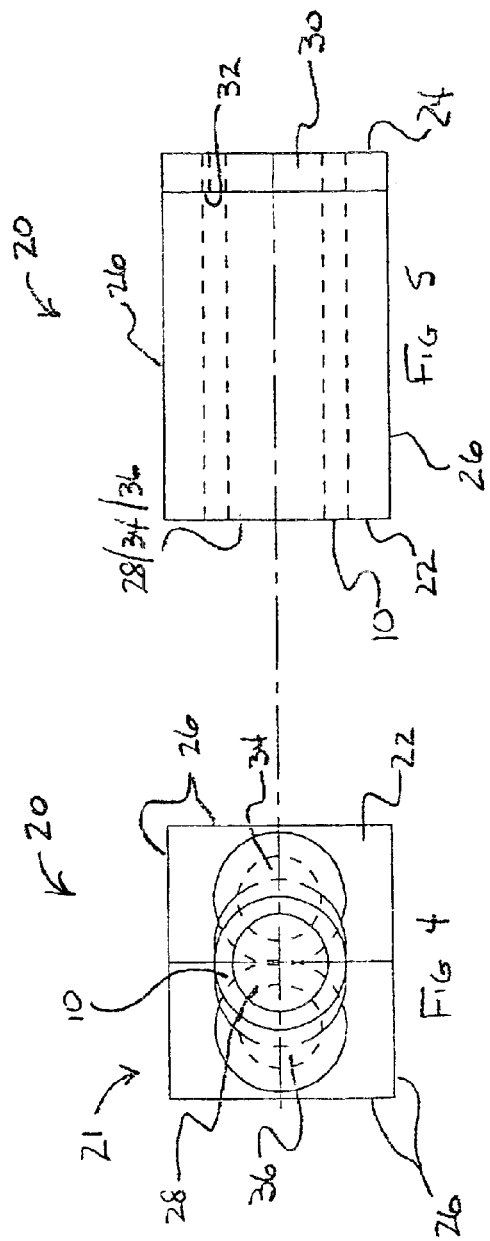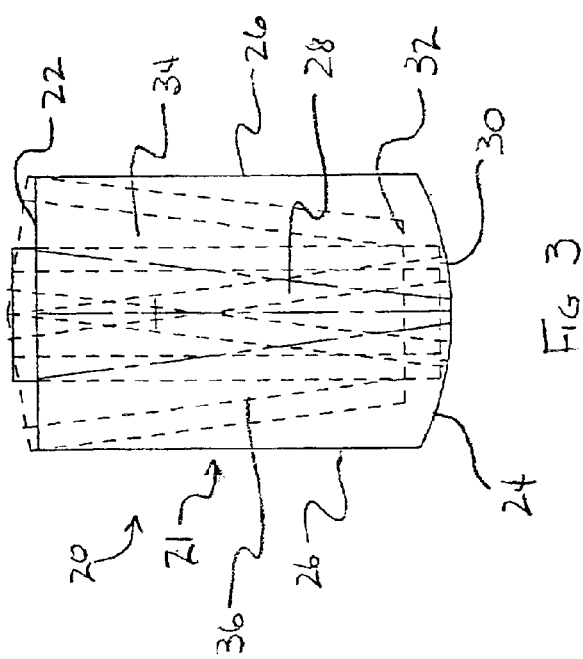

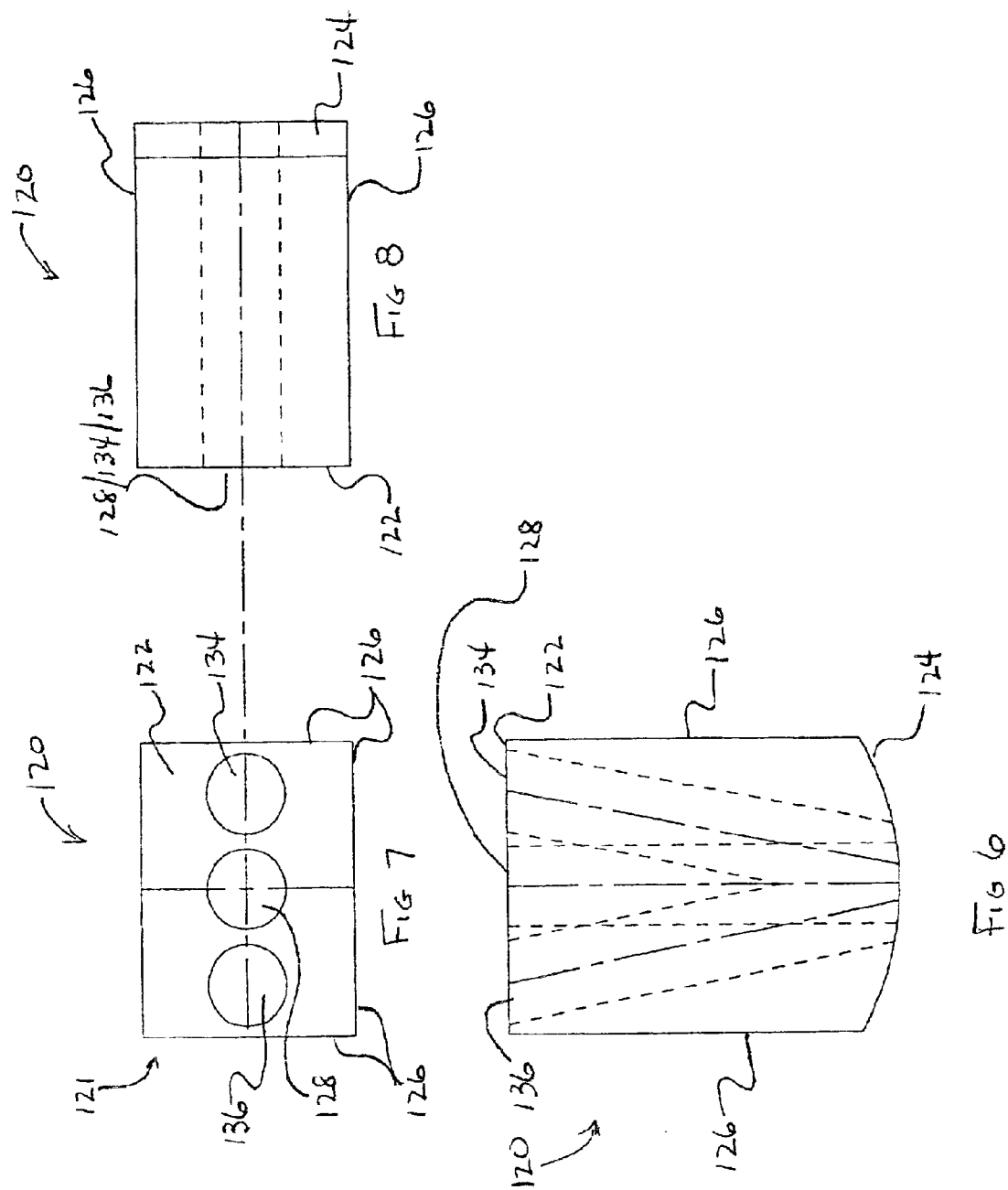

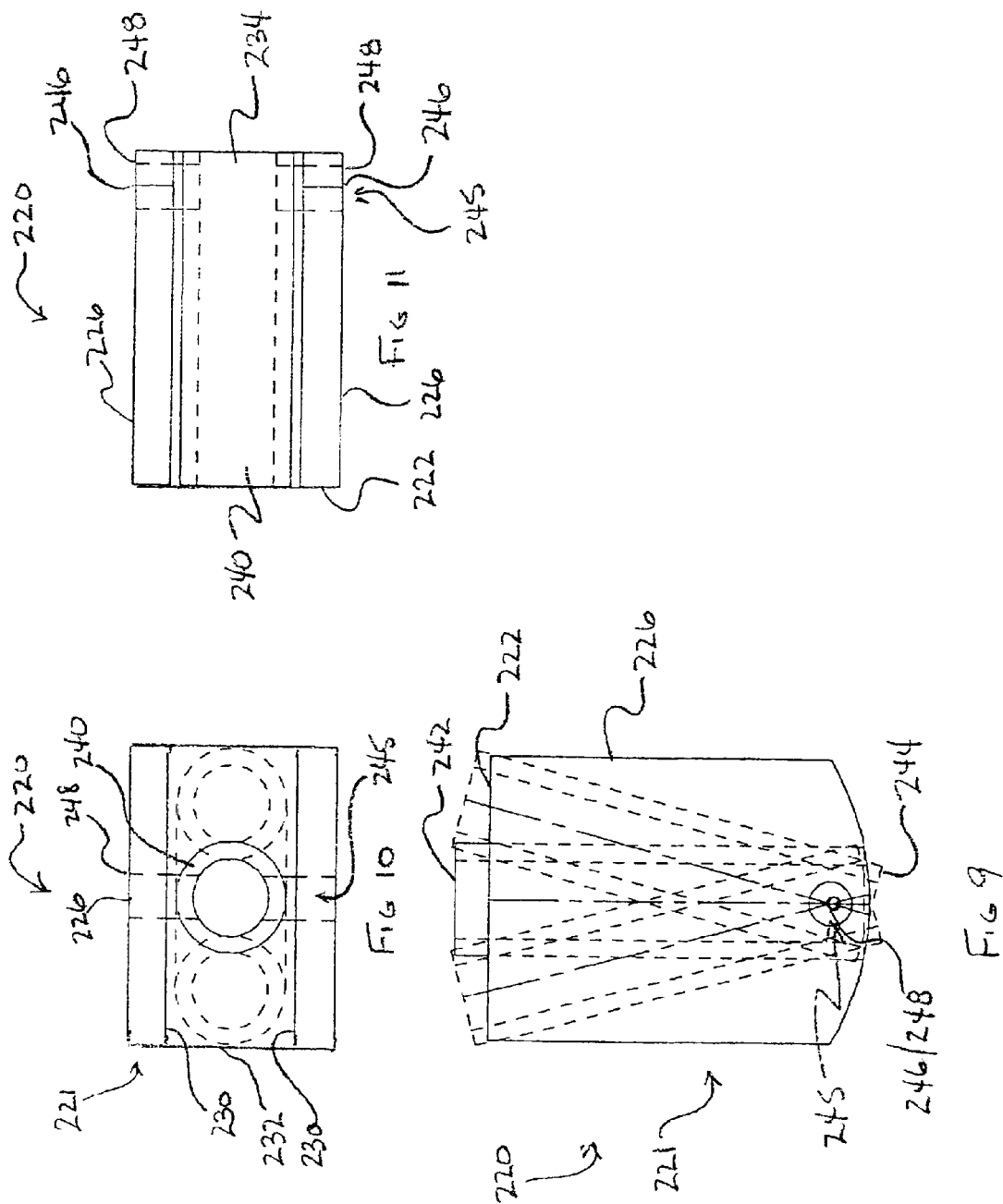

US 6,913,463 B2

DRILLING GUIDE FOR DENTAL IMPLANTATION

BACKGROUND OF THE INVENTION

1. Field of the Invention

The present invention relates to guides for drilling into a patient's jawbone for insertion of a dental implant. More particularly, the invention comprises a unique guide which allows for minor corrections in the angle and location of entry which are not typically possible with currently available guides.

2. Description of the Prior Art

In dentistry, it is often necessary to implant prosthetic devices, such as artificial teeth. This procedure requires the implantation of an anchor into the jaw, and then the attachment of the prosthetic to the anchor. Typically, the anchor is implanted by drilling into the jaw bone and screwing, or otherwise attaching the anchor into the bone. Proper alignment of the implanted anchor is necessary to ensure that the prosthetic aligns properly with the patient's natural teeth. One method of ensuring proper alignment of the anchor is by making an impression of the patient's mouth structure, fitting a drilling guide to the impression and creating a mold around the guide such that the mold may later be fitted to the patient's natural teeth. The primary drawback to this method lies in the existing art of the guides, in that only a single channel is provided for directing the drill. If the angle of that channel is off, even slightly, a good bone contact may not be possible. In this case, a new guide must be fitted, generally requiring a delay of the procedure, perhaps for several days. The present invention overcomes this problem by providing a plurality of channels so the angle may be altered should the need arise.

U.S. Pat. No. 5,851,207, issued to Morris D. Cesarone on Dec. 22, 1998, presents a FREELY SEPARABLE SURGICAL DRILL GUIDE AND PLATE, in which a drill guide is mounted a the tip of a manipulable forceps type tool. Unlike the present invention, alignment depends on the immediate judgement and steadiness of hand of the user.

U.S. Pat. No. 5,833,692, issued to Israel Abrahami on Nov. 10, 1998, presents a DRILL GUIDE having a locating pin which must be inserted into a hole drilled into a patients mandible and an adjustable guide block for guiding the drill. By contrast, the present invention requires no drilling into the mandible to secure the device and provides specifically aligned drilling paths.

U.S. Pat. No. 4,306,866, issued to Bernare Weissman on December 1981, presents an ADJUSTABLE DENTAL DRILL GUIDE wherein a drill guide is secured in a hole drilled into an adjacent tooth. By contrast, the present invention requires no drilling of healthy teeth for securing the guide.

U.S. Pat. No. 4,045,874, issued to Richard C. Roman on Sep. 6, 1977, presents a DENTAL DRILL GUIDE ATTACHMENT attachable directly to the dental drill. The guide of Roman is manually held in place on the work surface (tooth or mandible), while the guide of the present invention, is formed to a mold of the work surface and then transferred to the work surface in a secure manner, thereby allowing more precise drilling.

None of the above inventions and patents, taken either singly or in combination, is seen to describe the instant invention as claimed.

SUMMARY OF THE INVENTION

As has been previously stated, the implantation of oral prosthetics requires a drilling into the jaw bone at a relatively precise angle in order to implant an anchor device to which the prosthetic is attached. The present invention presents a drilling guide which enables the dentist or oral surgeon to drill at the precise angle, if not on a first attempt, at least without having to refit the patient with a second drilling guide. The present invention presents a guide having a plurality of guide paths by pivoting the stent to different angles, allowing for adjustment of the angle of attack for better alignment of the implant.

Accordingly, it is a principal object of the invention to provide a dental drilling guide which is economical to use.

It is another object of the invention to provide a dental drilling guide which is easy to install in a patients mouth.

It is a further object of the invention to provide a dental drilling guide which is easy to use.

Still another object of the invention is to provide a dental drilling guide which provides a precise angle of entry.

An additional object of the invention is to provide a dental drilling guide which allows for multiple angles of entry within a single guide unit It is again an object of the invention to provide a dental drilling guide which incorporates a depth guide in addition to angle guide.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein:

FIG. 1 is a plan view of the stent of the present invention.

FIG. 2 is an end view of the stent of FIG. 1.

FIG. 3 is a front view of a first embodiment of the alignment block of the present invention for use with the stent of FIGS. 1 and 2.

FIG. 4 is a plan view of the first embodiment of the alignment block of FIG. 3.

FIG. 5 is a side view of the first embodiment of the alignment block of FIG. 3.

FIG. 6 is a front view of a second embodiment of the alignment block of the present invention having integral stents.

FIG. 7 is a plan view of the second embodiment of the alignment block of FIG. 6.

FIG. 8 is a side view of the second embodiment of the alignment block of FIG. 6.

FIG. 9 is a front view of a third embodiment of the alignment block of the present invention having a single, pivotable stent.

FIG. 10 is a plan view of the third embodiment of the alignment block of FIG. 9.

FIG. 11 is a side view of the third embodiment of the alignment block of FIG. 9.

DETAILED DESCRIPTION OF THE PREFERRED EMBODIMENTS

The drilling guide of the present invention comprises two basic elements, a stent and a guide block, or in alternative embodiments a guide block having integral stent(s), each of which will be set forth individually hereinbelow.

Referring first to FIGS. 1 and 2, the stent 10 is depicted as being a hollow cylinder 12, having a smooth interior wall 14 and a striated exterior wall 16. The striations 18 are evenly spaced, circumferentially, along the length of cylinder 12, thereby providing a plurality of convenient points for adjusting the length of cylinder 12, and thus establishing a desired length of stent 10.

FIGS. 3 thru 11, collectively, depict three separate embodiments of guide block 20 which may be affixed to an occlusal surface of a jaw, typically by light curable resin or other means. The construction of each embodiment of guide block 20 will first be described, followed by a general description of the method of use for all of the embodiments.

Referring first to FIGS. 3 thru 6, guide block 20 has a substantially rectilinear block 21 having a proximal, substantially flat end 22 and a distal, slightly convex end 24, and four sides 26. A first round guide hole 28 is bored from a center point of proximal end 22, substantially parallel to the four sides 26, to a point at a predetermined distance from distal end 24. A round base guide hole 30, having a longitudinal axis coinciding with that of first guide hole 28 and a diameter slightly smaller than that of first guide hole 28 extends from the bottom of first guide hole 28 to distal end 24, thereby forming a stent stop 32 at the base of first guide hole 28, thereby preventing stent 10 from passing fully through guide block 20. A second round guide hole 34 and a third round guide hole 36, each having a diameter substantially equal to first guide hole 28, are bored from a point on first end 22 proximate each of two opposite sides 26, respectively, to stent stop 32 proximate the center of base guide hole 30, the centers of first guide hole 28, second guide hole 34 and third guide hole 36 being alined with one another. The three borings of first guide hole 28, second guide hole 34 and third guide hole 36 overlap such that each is open to the other along its length. Stent 10 is slidably insertable into any one of guide holes 28, 34 and 36 to a point of contact with stent stop 32.

While guide block 20 has been referred to as substantially rectilinear, it would evident to one skilled in the art that others shapes could be utilized with equal effectiveness. Likewise, while guide holes 28, 34, 36 have been referred to as substantially round, it would be evident to one skilled in the art that other shapes having a "regular perimeter" which hold stent 10 in a stable manner may also be used. For the purposes of this application, "regular perimeter" is defined as a circle or any other shape configured to hold a stent in a stable manner. It would be further evident to one skilled the art that the alignments of guide holes 28, 34, 36 may also vary slightly from the above without adversely affecting the concept of the invention. The above applies equally to the embodiments described hereinbelow.

Referring now to FIGS. 6 thru 8, guide block 120 is again a substantially rectilinear block 121 having a proximal, substantially flat end 122, a distal, slightly convex end 124, and four sides 126. A first round stent 128 is bored from a center point of proximal end 122 to a center point of distal end 124. A second round stent 134 and a third round stent 136, each having a diameter substantially equal to first stent 128, are bored from a point on proximal end 122 proximate each of two opposite sides 126, respectively, to a center point of distal end 124, the centers of first stent 128, second stent 134 and third stent 136 at first end 122 being alined with one another. First stent 128, second stent 134 and third stent 136 begin as individual borings at first end 122, but terminate at distal end 124, their axis intersecting at a single point.

Now moving to FIGS. 9 thru 11, guide block 220 is once again a substantially rectilinear block 221 having a proximal, substantially flat end 222 and a distal, slightly convex end 124, and four sides 226. A slot 228, presenting a substantially rectangular opening in proximal end 222, is formed in the interior of block 221. A pair of opposite walls 230 of slot 228 are formed substantially parallel to and spaced apart from two opposite sides 226 of block 221 and substantially normal to first end 222. A second pair of opposite walls 232 of slot 228 are formed substantially parallel to the remaining two opposite sides 226 of block 221, tapering inward and downward from the lines of abutment of first end 222 and sides 226 to a point proximate center of second end 224, terminating in a substantially rectangular opening 234 in distal end 224. Opening 234 has dimensions substantially equal to the diameter of a hollow, tubular stent 240 which is disposed within slot 228 such that a proximal stent end 242 extends slightly above proximal end 222 of block 221 while a distal stent end 244 extends to opening 234 in distal end 224 of block 221. Stent 240 pivots about a pivot 245 comprising a pair of pivot pins 246 disposed on opposite sides of stent 240 proximate distal stent end 244 and fitting into pivot holes 248 in the interior of slot 228 proximate opening 234. By pivoting about pivot pins 246, stent 240 may be angled from one extreme edge of proximal end 222 to the opposite, extreme edge of proximal end 222, thereby altering the angle at which distal stent end 244 is presented in relation to distal end 224 of block 221. It would be evident to one skilled in the art that pivot pins 246 and pivot holes 248 could be reversed such that pins 246 formed in slot 240 engage holes formed in stent 240 and that pivot pins 246 could be of a shape such as, but not limited to, hemispherical or similar, without departing from the spirit of the invention.

For simplicity of explanation of the method for using the drilling guide, the embodiment of FIGS. 1 thru 5 will be used, with variations described subsequently.

In preparation for dental implantation using prior art drilling guides or stents, an impression is typically made of a patient's mouth and a plaster cast made of the impression. A guide is formed to the plaster cast in such a way that it bridges between the teeth on either side of the implant site and the guide hole in the guide is aligned for the proper angle for drilling into the patient's jaw for implantation of an anchor for the prosthesis being fitted. The drilling guide is then transferred to the patient's mouth and bridged between the patient's own teeth, typically securing it with curable resins or plastics. The dentist or oral surgeon then places a dental drill into a stent the guide hole for drilling at the proper angle and at the proper depth. Heretofore, if the angle of drilling was not quite right, the entire fitting procedure had to be redone, causing delays in the implantation.

With the present invention the impression and casting are carried out as before and the drilling guide 20 is fitted to the casting, typically with a curable resin or plastic. Stent 10 is cut to the desired length at one of the striations 18 and then fitted into the central guide hole 28 until it strikes stent stop 32. The dentist then places the drill into the core of stent 32 and drills to the prescribed angle and depth. If he finds that the angle was not quite right, he withdraws stent 10 from central guide hole 28 and reinserts it into either guide hole 34 or 36 to adjust the drilling angle. On completion of the drilling, the drilling guide 20 is removed from the teeth.

In the second embodiment of FIGS. 6 thru 8, the same procedure is followed, with the exception that stent 110 is incorporated into drilling guide 120, as stents 128, 134 and 136. In the embodiment of FIGS. 9 thru 11 the pivotable stent 240 serves the same function of adjustability.

It is to be understood that the present invention is not limited to the embodiments described above, but encompasses any and all embodiments within the scope of the following claims.

What is claimed is:

1. A drilling guide kit for dental implantation comprising a substantially solid block having a proximal end and a distal end, said block being mountable to an occlusal surface of a jaw; and a stent comprising a striated exterior wall, said striations being spaced, circumferentially along the length of said stent, said striations adapted for cutting said stent to one of a plurality of different lengths, each of said plurality of different lengths defined by a predetermined number of successions of said striations.

2. A drilling guide kit for dental implantation comprising:
   a guide block, said guide block comprising a substantially solid block having a proximal end and a distal end, said guide block mountable to an occlusal surface of a jaw,
   said guide block having therein a plurality of channels for positioning a single stent therein at a plurality of different angles, thereby enabling a practitioner to use a single guide block to position, at any of a variety of angles, the drill for a dental implant intended for a specific position in the mouth without repositioning the guide block,
   wherein said plurality of channels comprises:
      a first channel having a regular perimeter and a length along a longitudinal axis, said length extending from said proximal end to said distal end, and at least one secondary channel, each of said at least one secondary channel having a regular perimeter and a length along a longitudinal axis, each of said at least one secondary channel, respectively, extending at an angle, along said longitudinal axis, different from that of said first channel, through said guide block, and wherein at least one of said at least one secondary channel intersects said first channel proximate said distal end of said guide block,
   further comprising a stent stop, said stent stop comprising a ledge formed interior of said first channel proximate said distal end of said guide block;
   and a stent, said comprising a hollow cylinder having a predetermined length.

3. A method for drilling for a dental implant using a guide block comprising:
   providing a guide block having a plurality of guide holes therein,
   fixing said guide block to a patient's teeth in a first position,
   positioning a drill within said guide block and checking alignment of said drill to determine that said alignment is proper for a desired drilling angle and depth of a particular tooth socket,
   adjusting alignment of said drill to correct any errors in the drill angle relative to said tooth socket as required, said adjustment being achieved by removing said drill from one guide hole and positioning it in another guide hole without removing or repositioning said drilling guide means from its first position,
   rechecking alignment of said drilling guide to determine that said adjusted alignment is correct,
   drilling at a desired angle utilizing said drilling guide, and
   removing said drilling guide from said patient's mouth.

4. A method for drilling for a dental implant using a drilling guide, as defined in claim 3, wherein said providing step comprises providing a guide block that includes:
   a stent comprising a hollow cylinder, said cylinder having a smooth interior wall and a predetermined length;
   a first one of said plurality of guide holes having a regular perimeter and a length along a longitudinal axis, said length extending from said proximal end to said distal end,
   and a stent stop, said stent stop comprising a ledge formed interior of said first guide hole proximate said distal end of said guide block;
   said plurality of guide holes comprising at least one secondary guide hole, each of said at least one secondary guide hole having a regular perimeter substantially equal to said regular perimeter of said first guide bole and a length along a longitudinal axis, each of said at least one secondary guide hole, respectively, extending at an angle, along said longitudinal axis, different from that of said first guide hold, through said guide block;
   said stent adapted for insertion into any one of said guide holes for guiding a dental drill at a predetermined angle, said angle determined by the one of said guide holes into which said stent is inserted.

5. A method for drilling for a dental implant using a drilling guide, as defined in claim 3, wherein said providing step comprises providing said guide block in the form of a substantially solid block having a proximal end and a distal end, wherein said plurality of guide holes comprises:
   a first bore having a regular perimeter and a length along a longitudinal axis, said bore extending through said guide block from said proximal end to said distal end, and
   at least one secondary bore, each of said secondary bores comprising a bore having a regular perimeter substantially equal to said regular perimeter of said first bore and a length along a longitudinal axis, each of said at least one secondary bore, respectively, extending through said guide block, at an angle different from that of said first bore;
   each of said bores being adapted for guiding a dental drill at a predetermined angle.

* * * * *